United States Patent [19]
Yumoto

[11] Patent Number: 5,893,861
[45] Date of Patent: Apr. 13, 1999

[54] SURGICAL KNIFE FOR CUTTING OUT TENDON SHEATH

[76] Inventor: Yoshiji Yumoto, 1455-4, Hachimanmae, Koyama, Suzaka-shi, Nagano, 382, Japan

[21] Appl. No.: 08/817,538
[22] PCT Filed: Sep. 17, 1996
[86] PCT No.: PCT/JP96/02668
  § 371 Date: Apr. 23, 1997
  § 102(e) Date: Apr. 23, 1997
[87] PCT Pub. No.: WO97/10761
  PCT Pub. Date: Mar. 27, 1997

[30] Foreign Application Priority Data

Sep. 19, 1995 [JP] Japan .................. 7-239549

[51] Int. Cl.$^6$ .................................................. A61B 17/32
[52] U.S. Cl. ............................................ 606/167; 606/170
[58] Field of Search .................................. 606/167, 170

[56] References Cited

U.S. PATENT DOCUMENTS

| | | | |
|---|---|---|---|
| 1,037,693 | 9/1912 | Watson | 606/167 |
| 5,282,816 | 2/1994 | Miller et al. | 606/167 |
| 5,628,760 | 5/1997 | Knoepfler | 606/167 |
| 5,681,262 | 10/1997 | Isse | 606/167 |

FOREIGN PATENT DOCUMENTS 3-141939  6/1991  Japan .

*Primary Examiner*—Michael Buiz
*Assistant Examiner*—Daphna Shai
*Attorney, Agent, or Firm*—Birch, Stewart, Kolasch & Birch, LLP

[57] ABSTRACT

A surgical knife of the present invention can be safely and correctly used for cutting open tendon sheaths so as to treat trigger fingers, so the surgical knife comprises: a shaft section (12) being extended from a grip section (10); a blade section (14) being sidewardly extended from a side face of the shaft section (12); and a guide section (16) being sidewardly extended, in the direction the same as the extended direction of the blade section (14), from a lower part of the blade section (14), wherein the blade section (14) includes: an arc blade (K) being provided in a connecting part to the guide section (16) and being formed into an arc shape which is smoothly connected to the guide section (16); and a linear blade (J, H) being linearly formed and parallel to the shaft section (12).

10 Claims, 4 Drawing Sheets

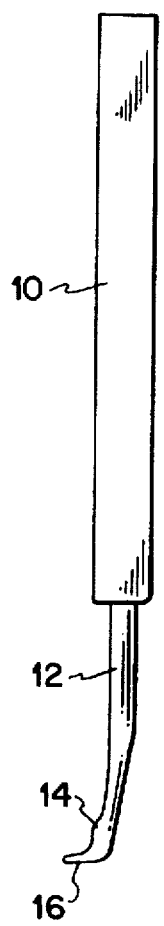
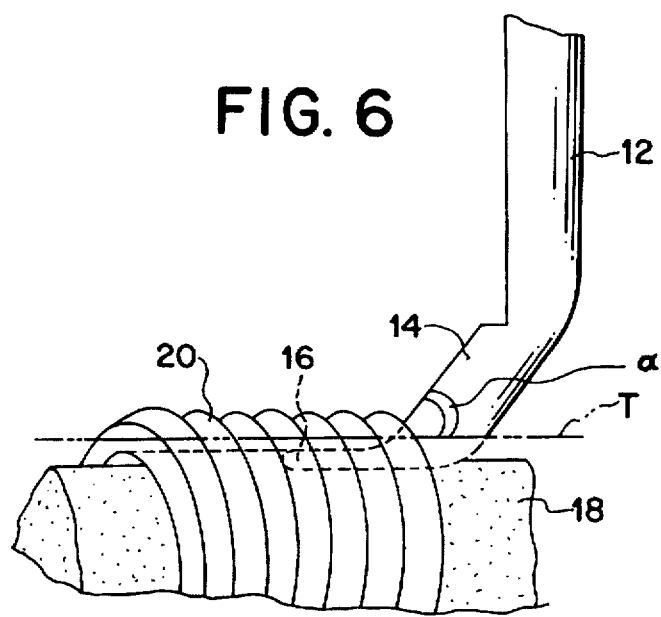
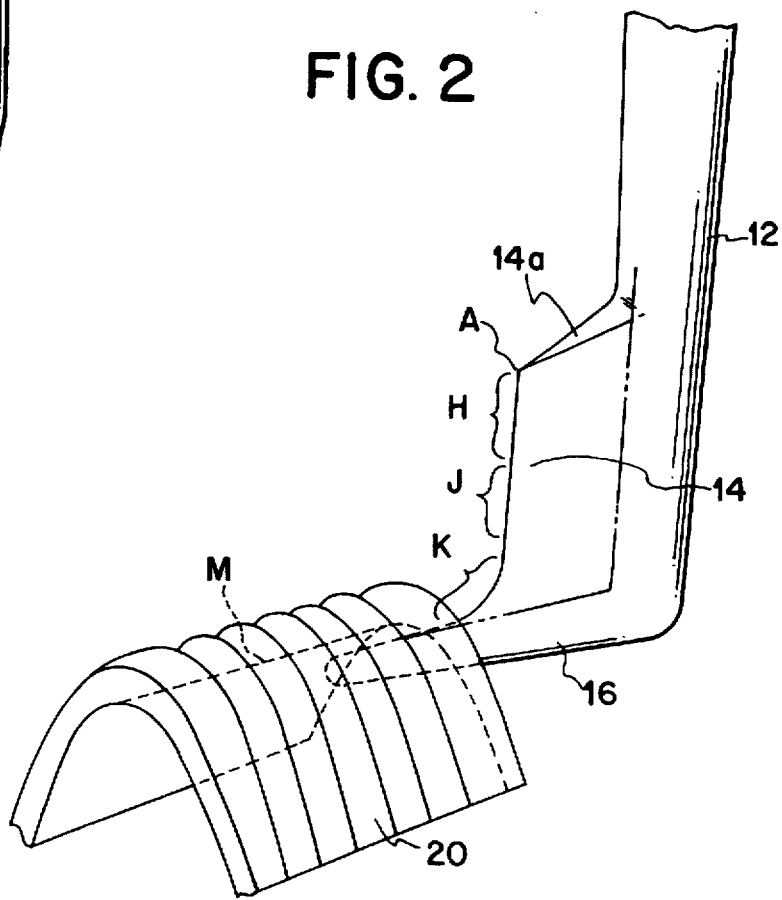

SURGICAL KNIFE FOR CUTTING OUT TENDON SHEATH

FIELD OF TECHNOLOGY

The present invention relates to a surgical knife, more precisely relates to a surgical knife for cutting out a tendon sheath so as to treat for so-called trigger fingers, etc.

BACKGROUND OF TECHNOLOGY

The inventor of the present invention has invented a surgical knife for cutting out a tendon sheath so as to treat for trigger fingers (see Japanese Patent Publishing Gazette No. 5-55136). A trigger finger means a finger, which cannot smoothly bend and stretch, and it is kept in a bending state when it is bent or stretched until reaching a prescribed angle; it springs back when it is further bent or stretched. Trissen fingers can be treated by cutting out tendon sheaths. The tendon sheath encloses a flexor tendon for bending and stretching a finger, so the damaged finger can be smoothly moved by cutting out the tendon sheath.

A conventional surgical knife is used for cutting out the tendon sheath, and it can be properly used for a normal skin incisional operation and a minimal skin incisional operation. FIG. 10 shows a side view of the conventional surgical knife for cutting out the tendon sheath; FIG. 11 shows an enlarged view of a blade section thereof. The surgical knife comprises: a grip section 10; a shaft section 12 being attached to the grip section 10; a blade section 14 being slightly extended from a side face of a front end section of the shaft section 12; and a guide section 16 being extended, in the same direction as the extended direction of the blade section 14, from a lower end of the blade section 14.

To use the surgical knife, as shown in FIG. 12, a front end of the guide section 16 is introduced into a space between a flexor tendon 18 and a tendon sheath 20, and the tendon sheath 20 is gradually cut out by sliding the guide section 16 on the flexor tendon 18. In the case of the minimal skin incisional operation, skin immediately above the tendon sheath is slightly cut to insert the blade section 14 of the surgical knife.

SUMMARY OF THE INVENTION

In the above described surgical knife, the cutting direction of the blade section 14 is guided by the guide section 16, so the surgical operation can be correctly and safely executed without cutting the flexor tendon even in the case of the minimal skin incisional operation in which an affected part cannot be directly seen. However, it is important for safe surgical operation to visually see the cutting part of the tendon sheath. The surgical knife is abraded by frequent use, so the knife must be ground to keep it sharp; the blade section of the surgical knife will therefore be thinner and its durability will be lower. Therefore, a surgical knife having high sharpness and high durability is required.

An object of the present invention is to provide a surgical knife, which is capable of correctly and safely cutting out the tendon sheath and which has high cutting quality and high durability.

To achieve the object, the present invention has the following constitutions.

The surgical knife for cutting out a tendon sheath, comprises: a grip section; a shaft section being extended from a lower end of the grip section; a blade section being sidewardly extended from a side face of a lower part of the shaft section; and a guide section being extended from a lower end of the blade section in the same direction as the extended direction of the blade section, characterized in that the blade section includes: an arc blade being provided in a connecting part between the guide section and the blade section, the arc blade being formed into an arc shape; and a linear blade being linearly formed between the arc blade and an upper end of the blade section, the linear blade being parallel to the shaft section. The arc blade has high sharpness or high cutting quality; the linear blade assists the arc blade to cut. Since the linear blade is made parallel to the shaft section and its blade angle is wide, the operation can be executed without widely cutting the skin.

If the grip section is formed into a thin and long rectangular parallelepiped block, the grip section can be securely gripped, so that the surgical knife can be more correctly and safely used.

If the shaft section is formed into a thin needle, the surgical knife can be easily introduced into the affected part to be operated.

If the guide section is formed into an L-shape with respect to the shaft section and formed thinner toward the front end, the tendon sheath can be easily searched, and the surgical knife can be easily guided to execute correct operation.

If an upper end of the blade section is extended from the side face of the shaft section like a step, the position of the blade section can be correct during the operation.

If an upper end face of the blade section is formed into a flat face parallel to the guide section, or the upper end face of the blade section is formed into a triangle shape, whose sharpened apex is included in the linear blade, the sharpened apex can be visually seen, so that the position of the blade section is proper in order to execute safe operation.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

FIG. 1 is a side view of a surgical knife of the present invention;

FIG. 2 is an enlarged view of a blade section of the surgical knife;

FIG. 6 is an explanation view showing blade angle of the blade section;

DESCRIPTION OF THE PREFERRED EMBODIMENTS

Preferred embodiments of the surgical knife of the present invention will be explained.

Figure 10:
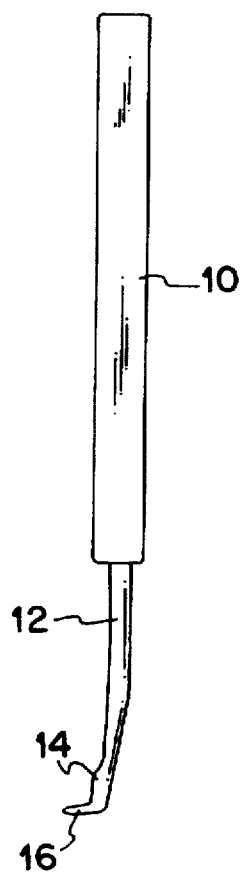
FIG. 10 is a side view of the conventional surgical knife.
Figure 11:
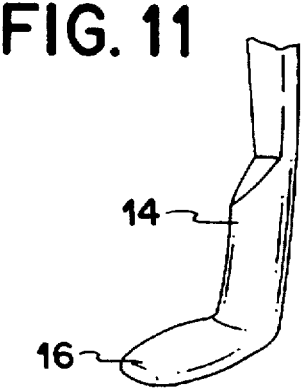
FIG. 11 is an enlarged view of a blade section of the conventional surgical knife.
Figure 12:
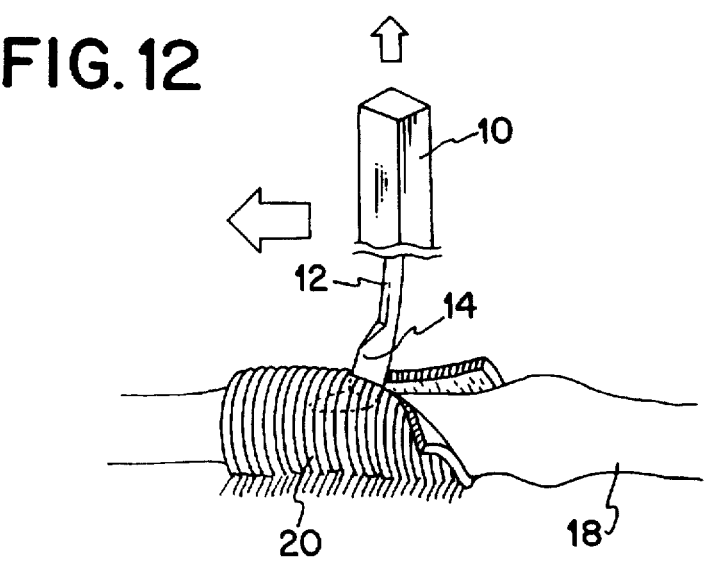
FIG. 12 is an explanation view showing action of the conventional surgical knife.

FIG. 1 is the side view of an embodiment of the surgical knife of the present invention. The surgical knife of the present embodiment comprises: a grip section 10; a shaft section 12; a blade section 14; and a guide section 16, as well as the conventional surgical knife shown in FIG. 10. A feature of the surgical knife of the present embodiment is a structure of the blade section 14 as shown in FIG. 2, namely the blade section 14 includes: an arc blade, which is formed into an arc shape, being provided in a connecting part between an upper face of the guide section 16 and a base of the blade section 14; and a linear blade being linearly formed between an upper end of the arc blade and an upper end of the blade section, the linear blade being almost parallel to the shaft section 12.

Figure 3:
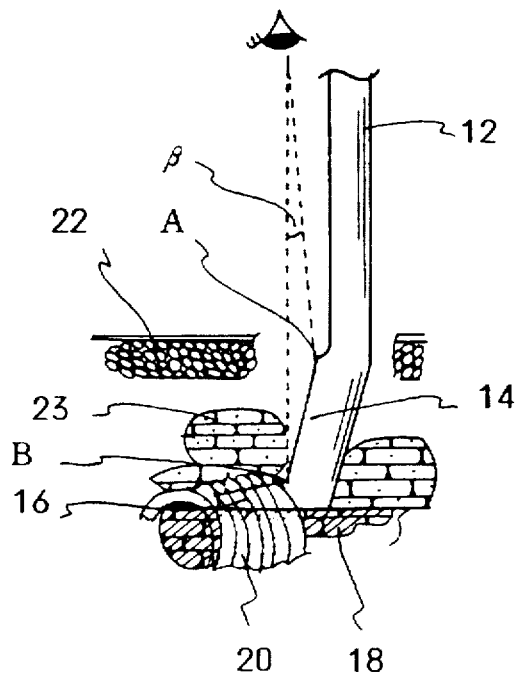
FIG. 3 is an explanation view showing action of the surgical knife in the minimal skin incisional operation.
Figure 4:
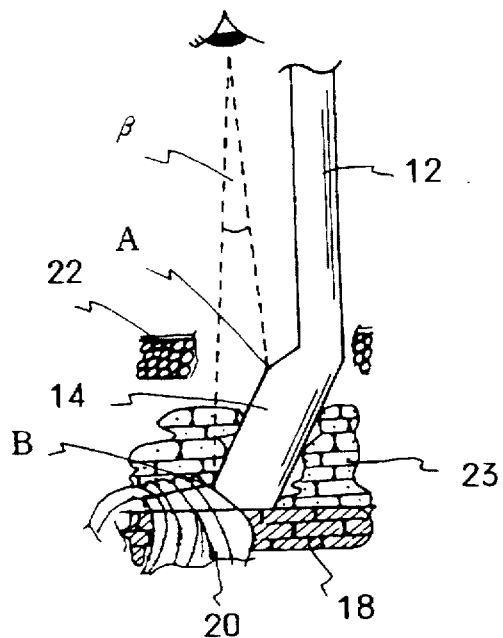
FIG. 4 is an explanation view showing action of the surgical knife in the minimal skin incisional operation.
Figure 5:
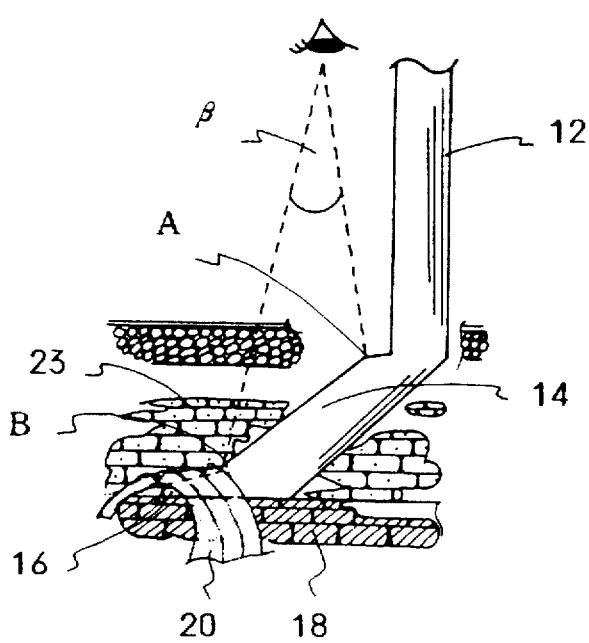
FIG. 5 is an explanation view showing the action of the surgical knife in the minimal skin incisional operation.

FIGS. 3–5 are explanation views showing action of the surgical knife in the minimal skin incisional operation, in each of which the blade angle of the blade section 14 is different. FIGS. 3, 4 and 5 shows the cases where the angle between the linear blade and the guide section 16, is 80°, 75° and 45°, respectively.

Each drawing shows the cases of the minimal skin incisional operation, so the outer skin 22 is cut, and the surgical knife is inserted into the cut part so as to cut out the tendon sheath 20. Since the skin is minimally cut in the minimal skin incisional operation, an operation doctor determines a part of the tendon sheath 20 to be cut out by touching, then he or she slightly cuts the outer skin 22 immediately above the part to introduce the surgical knife thereinto.

To cut out the tendon sheath 20 with the surgical knife, the guide section 16 is introduced into a space between the flexor tendon 18 and the tendon sheath 20, then the blade section 14 is moved and guided by the guiding section 16. To enter the guide section 16 into the tendon sheath 20, an entrance of the tendon sheath 20 must be found with the guide section 16, but the entrance is covered with subcutaneous fat, etc. so it cannot be seen visually. But a tendon can be found by carefully touching a surface of the outer skin, so the guide section 16 is headed in the running direction of the tendon and slid on a surface of the tendon; the guide section can be entered into the entrance of the tendon sheath. Entering the guide section 16 in the tendon sheath can be determined by resistance, which is caused by hanging the surgical knife upward. In the case of a tendon sheath of standard thickness, the tendon sheath 20 is cut out by the base of the blade section 14 as shown.

In the case of the minimal skin incisional operation, the tendon sheath 20 cannot be directly visually seen, so the tendon sheath 20 can be found by inserting an imitation knife, whose shape is equal to the surgical knife but whose blade section 14 has no blade, into a cut part in the outer skin 22; the entrance of the tendon sheath 20 can be found. When the entrance of the tendon sheath is found, the doctor changes the knife from the imitation knife to the surgical knife while keeping the same finger positions on the grip section, then he or she inserts the guide section 16 to the position, where the imitation knife had been inserted, and cuts the tendon sheath 20.

As shown in FIG. 6, the tendon sheath 20 runs in the direction "T", so the guide section 16 is moved parallel to the direction "T". In the present invention, an angle "α" with respect to the line "T" is called the "blade angle", and the maximum angle of the blade angle is 90°.

When the blade section 14 cuts out the tendon sheath 20, if the blade angle is greater or the blade is more parallel to the shaft section 12, the cutting quality of the surgical knife is worse. In the cases shown in FIGS. 3–5, the cutting quality of the surgical knife shown in FIG. 5 is the best; the cutting quality shown in FIG. 3 is the worst. In the case of the surgical knife having good cutting quality, the cutting quality remains good even if it is abraded, so it has good durability. On the other hand, in the case of the surgical knife having a greater or wider blade angle, the cutting quality is worse even if the blade is slightly abraded, so it does not have good durability.

In the case when the blade section 14 has a narrow blade angle, the surgical knife has high cutting quality so there is a risk of damaging blood vessels or nerves while cutting out the tendon sheath 20. On the other hand, in the case of the greater or wider blade angle, the surgical knife does not have high cutting quality so the blade does not damage elastic tissues, e.g., nerves, as far as the surgical knife is used with usual care.

As shown in FIGS. 1 and 2, a connecting section between an upper end of the blade section 14 and a lower end of the shaft section 12 is formed into a step 14a, and the step 14a is very important for the surgical operation.

In the case of the minimal skin incisional operation, the cut part of the tendon sheath 20, which is cut by the blade section 14, cannot be directly visually seen while cutting out the tendon sheath 20. Since the outer skin 22 is slightly cut in the minimal skin incisional operation, the outer skin 22 covers over the operating area to be treated. In the case of the normal skin incisional operation too, some subcutaneous fat around the operating area covers over the part of the tendon sheath 20 which is cut out by the blade section 14 even if the operating area is opened by a retractor 24; the operating area cannot be directly visually seen, either.

In any cases, if the cutting part of the tendon sheath 20, which is cut out by the blade section 14, cannot be visually seen at all, the surgical operation cannot be correctly executed without risks. Therefore, a sharpened apex of the step 14a of the blade section 14 can be visually seen, and the cutting position, which is being cut by the blade section 14, can be determined on the basis of the position of the apex. When the apex (A) of the blade section 14 and a cutting position (B) of the blade section 14 are visually known, if a visual angle "β" between the points "A" and "B" is wider, it is difficult to know the cutting position; if the visual angle "β" is narrower, the cutting position can be correctly known. In the cases shown in FIGS. 3–5, the surgical knife shown in FIG. 3, in which the blade is arranged most parallel to the shaft section 12, is the most useful surgical knife because the cutting position can be known correctly.

Even if the guide section 16 is covered with the subcutaneous fat, the step 14a of the blade section 14 can be seen, so depth of the guide section 16 can be known by the visual position of the step 14a, and the surgical knife can be correctly and safely used.

Figure 7:
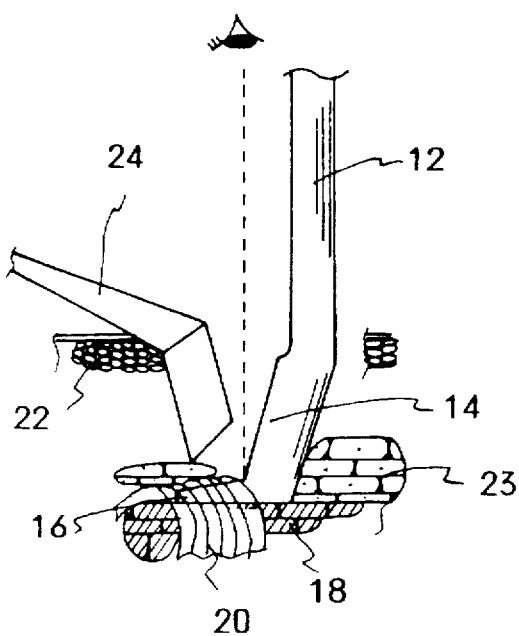
FIG. 7 is an explanation view showing action of the surgical knife in the normal skin incisional operation.
Figure 8:
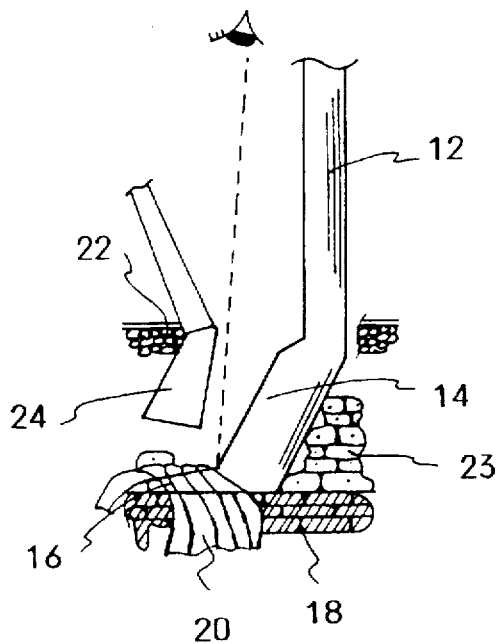
FIG. 8 is an explanation view showing action of the surgical knife in the normal skin incisional operation.

FIGS. 7 and 8 show the cases of the normal skin incisional operation, in each of which the blade angle of the surgical knife is different. In the normal skin incisional operation, the skin is cut and opened broadly, and fat tissues are opened by the retractor 24. In FIG. 7, the outer skin 22 is cut out, the cut part is kept open by the retractor 24, then the tendon sheath 20 is cut out by the surgical knife. In the normal skin incisional operation, the flexor tendon 18 and the tendon sheath 20 can be directly visually seen, so the guide section 16 is inserted into the entrance of the tendon sheath 20, and the tendon sheath 20 is cut out by the blade section 14.

In the normal skin incisional operation, the blade section 14 having a narrower blade angle has a higher cutting quality and higher durability as well as the minimal skin incisional operation. If the blade is arranged close to a right angle with respect to the guide section 16, the cutting position of the the blade section 14 can be known correctly, so correct and safe operation can be executed.

In the normal skin incisional operation, the lower part of the blade section 14 is sometimes covered with the subcutaneous fat 23, etc. and cannot be seen while cutting the tendon sheath 20 as well as the minimal skin incisional operation. But the depth and the position of the blade section 14 can be determined on the basis of the apex (A) of the step 14a of the blade section 14, so the surgical knife can be used without unnecessary cutting and unnecessary movement of the guide section 16.

Figure 9:
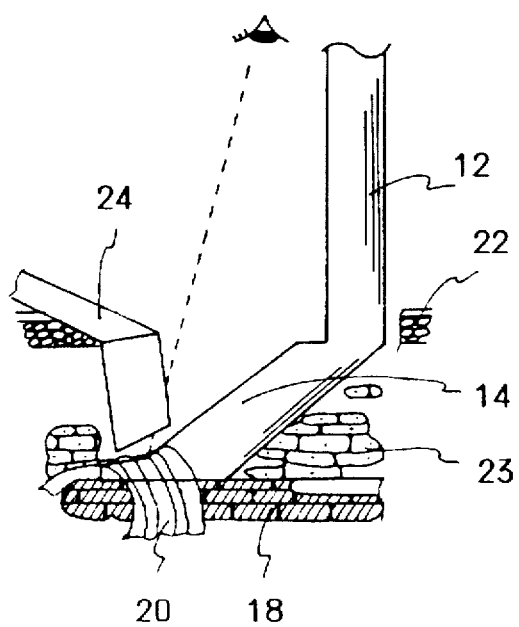
FIG. 9 is an explanation view showing action of the surgical knife in the normal skin incisional operation.

Skin is cut and opened in the normal skin incisional operation, if the blade of the blade section 14 is formed nearly parallel to the shaft section 12 as shown in FIGS. 7 and 8, the cut part of the skin can be small; if the blade angle thereof is greater or wider as shown in FIG. 9, the cut part of the skin, from which the surgical knife is inserted, must be broader.

In the conventional surgical knife for the minimal skin incisional operation and the normal skin incisional operation, the blade angle is made narrower to increase the cutting quality and the durability; the blade angle is made wider to correctly know the present cutting position and execute the surgical operation safely.

The mutually contrary conditions can be satisfied with the surgical knife of the present invention.

In FIG. 2, the blade is formed on a sharpened edge of the blade section 14, and it is divided into three parts: a base part "K" provided in a connecting part between the guide section 16 and the blade section 14; a mid part "J"; and an upper part "H". The part "K" is formed into an arc shape and connects the upper face of the guide section 16 with the lower end of the blade section 14; the parts "K" and "J" are linearly smoothly continued.

The parts of the blade section 14 will be explained.

The part "K" is a main cutting part for actually cutting out the tendon sheath 20. Since the part "K" is formed into the arc shape as an arc blade, the blade angle of the blade entering the tendon sheath 20 is narrower than the example shown in FIG. 5, so the tendon sheath 20 can be sharply cut out, and its cutting quality can be quite higher.

To cut out the tendon sheath 20, the guide section 16 is introduced into a space between the tendon sheath 20 and the flexor tendon, then the surgical knife is pulled upward and pushed forward to cut out. With this action, the blade section 14 is moved along the inner highest part (M) of the tendon sheath 20, and it cuts out the tendon sheath 20. The tendon sheath 20 is cut out by the arc blade or the part "K".

The part "J" is formed above the part "K", but a thin tendon sheath 20, e.g., a child's tendon sheath, can be cut out by the part "K" only. However, in the cases of cutting a thick tendon sheath, e.g., a thick trigger finger, de Quervain's disease, the part "J" cooperates to cut out the thick tendon sheath. In the case of cutting the thick tendon sheath too, the thick tendon sheath is primarily cut by the part "K" so the cutting quality of the surgical knife can be kept high.

The part "H" usually does not cooperate to cut out, but some flexible tendon sheath 20 is risen upward when it is cut out. In this case, the part "H" cuts out the risen tendon sheath. By using the surgical knife for a long time, the part "J" is abraded, so an actual cutting part is moved from the part "J" to the part "H", so the both parts act as a linear blade. By the change of the actual cutting part, the surgical knife can be used for a long time without grinding the blade. The apex (A), which is located at an upper end of the part "H", is used, as a visual standard position, to visually measured the depth of the blade section 14 and to know the present cutting position of the blade section 14.

Since the surgical knife of the present embodiment has above described structure, the cutting quality of the blade section 14 can be effectively improved, and the actual cutting position of the blade section 14 can be quite close to the visual standard position by forming the parts "J" and "H" almost parallel to the shaft section 12 so that the present cutting position can be correctly known and the surgical operation can be executed safely. Even if the part "J" or "H" contacts blood vessels or nerves, they are not severely damaged so the surgical knife of the present embodiment can be used properly.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A surgical knife for cutting out a tendon sheath, comprising:

a grip section;

a shaft section being extended in a generally longitudinal direction from a lower end of said grip section;

a blade section being extended from a side face of a lower part of s aid shaft section in a generally orthogonal direction; and a guide section being extended from a lower end of said blade section in a direction the same as the extended direction of said blade section wherein said blade section includes:

an arc blade being provided in a connecting part between said guide section and said blade section, said arc blade being formed into an arc shape; and a linear blade being linearly formed between said arc blade and an upper end of said blade section, said linear blade being parallel to said shaft section.

2. The surgical knife according to claim 1, wherein said grip section is formed into a thin and long rectangular parallelepiped block.

3. The surgical knife according to claim 1, wherein said shaft section is formed into a thin needle.

4. The surgical knife according to claim 1, wherein said guide section is formed into an L-shape with respect to said shaft section, said guide section is formed thinner toward a front end.

5. The surgical knife according to claim 1, wherein an upper end of said blade section is extended from the side face of said shaft section in said generally orthogonal direction to form a step.

6. The surgical knife according to claim 5, wherein said upper end of said blade section is formed into a flat face parallel to said guide section.

7. The surgical knife according to claim 6, wherein the upper end of said blade section is formed into a triangle shape, whose sharpened apex is included in said linear blade.

8. The surgical knife according to claim 1, wherein a thickness of said blade section in said generally orthogonal direction is greater than a thickness of said shaft section in said generally orthogonal direction.

9. The surgical knife according to claim 1, wherein said shaft section and an upper end of said blade section form an L-shape.

10. The surgical knife according to claim 1, wherein an edge of said arc blade curves from said generally longitudinal direction to said generally orthogonal direction, said guide section extending from said arc blade in said generally orthogonal direction in a substantially straight line.

* * * * *